United States Patent [19]
Young

[11] 3,988,234
[45] Oct. 26, 1976

[54] SODIUM SPECIFIC GLASS ELECTRODES
[75] Inventor: Chung Chang Young, Toledo, Ohio
[73] Assignee: Owens-Illinois, Inc., Toledo, Ohio
[22] Filed: Oct. 3, 1974
[21] Appl. No.: 511,720

[52] U.S. Cl. .............................. 204/195 G; 106/52
[51] Int. Cl.² ......................................... G01N 27/36
[58] Field of Search ............... 204/1 T, 195 G, 1 A; 106/52

[56] References Cited
UNITED STATES PATENTS

| | | |
|---|---|---|
| 2,444,845 | 7/1948 | Perley .............................. 204/195 G |
| 2,829,090 | 4/1958 | Eisenman et al. .............. 204/195 G |
| 3,410,777 | 11/1968 | Ross ................................ 204/195 G |
| 3,459,641 | 8/1969 | Hebert ............................ 204/195 G |
| 3,713,992 | 1/1973 | Akazawa ......................... 204/195 G |
| 3,804,646 | 4/1974 | Dumbaugh ............................ 106/52 |

OTHER PUBLICATIONS

Perley "Analytical Chemistry", vol. 21, No. 3, Mar. 1949, pp. 391–394.

*Primary Examiner*—T. Tung
*Attorney, Agent, or Firm*—Howard Bruss; E. J. Holler; Richard B. Dence

[57] ABSTRACT

The present invention concerns sodium silicate and sodium aluminosilicate glass compositions which contain specified proportions of tantalum oxide and glass electrodes made therefrom, which are particularly sensitive to sodium ions in aqueous solutions containing sodium ions and other monovalent cations. These glasses represent an improvement over sodium aluminosilicate glass electrodes of the type disclosed in U.S. Pat. No. 2,829,090.

2 Claims, 1 Drawing Figure

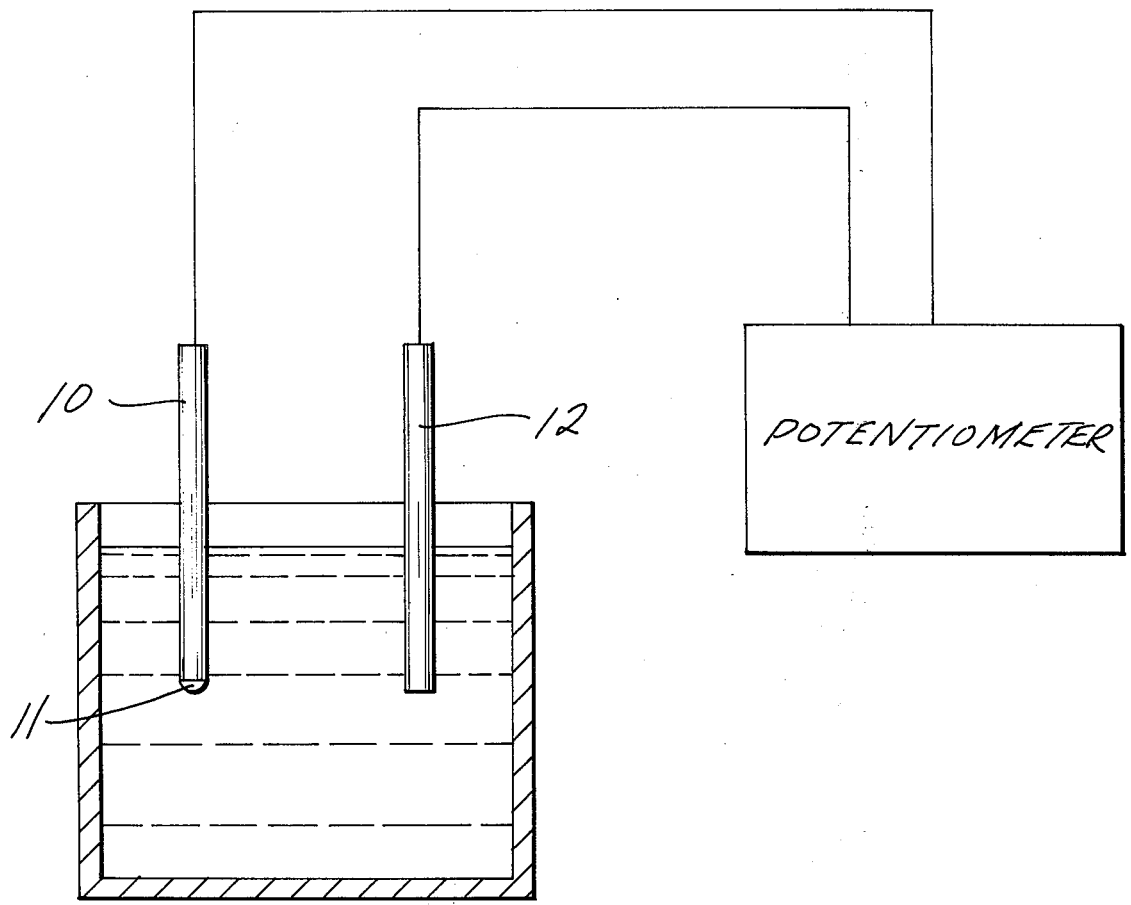

SODIUM SPECIFIC GLASS ELECTRODES

The problem of determining sodium ions in aqueous solutions containing sodium ions and other monovalent cations is well known in the analysis of specimens of industrial and medical interest, and there has been a great deal of research work directed to the design and manufacture of electrodes for carrying out such determinations. In the past various ion selective glass electrodes have been reported and the following patents and publications are believed to be representative of the state-of-the-art in this field. "Glasses for Measurements of pH" by George A. Perley, Analytical Chemistry, 21, No. 3 (1949) pp. 394–401; "Glass Electrode for Measuring Sodium Ion" by George Eisenman, Donald O. Rudin, and James U. Casby, Science, 126, (1957) pp. 831–834; "The Behaviour of the Glass Electrode in Connection with its Chemical Composition" by B. Lengyel and E. Blum, Faraday Society Transactions, 30, (1934) pp. 461–471; "Composition of pH-Responsive Glasses" by George A. Perley, Analytical Chemistry, 21, No. 3 (1949) pp. 391–394; U.S. Pat No. 3,041,252; U.S. Pat. No. 3,450,604; U.S. Pat No. 3,459,641; U.S. Pat. No. 2,444,845; U.S. Pat. No. 3,713,992; and U.S. Pat. No. 2,497,235.

One of the more practical glass electrodes to date is disclosed in U.S. Pat. No. 2,829,090 which provides a glass electrode for selectively measuring sodium ions in ionic mixtures including potassium and hydrogen ions wherein the electrode comprises a soda alumina silicate glass having the ratio of the mole % of alumina to soda of at least 1 to 1. The particularly preferred composition of this patent contains 11 mole % soda, 18 mole % alumina, and 71 mole % silica.

The sensitivity of the electrode glass in measuring sodium ions with respect to other monovalent cations is described in terms of the equation used in U.S. Pat. No. 2,829,090 which is set forth below.

$$E = E° + \frac{RT}{F}\ln\ [(A^+)^{1/n_{AB}} + k_{AB}{}^{1/n}AB\ (B^+)^{1/n}\ AB]^{n_{AB}}$$

wherein:
E = measured E.M.F.
E° = standard potential
R = ideal gas equation constant
T = temperature (absolute)
F = Faraday constant
$(A^+)$ and $(B^+)$ = activity of the ionic species $A^+$ and $B^+$
$n_{AB}$ and $k_{AB}$ = empirical constants for a given glass composition and ionic pair $A^+$ and $B^+$.

This equation is widely used in describing sodium specific electrodes and will be used in presenting data and properties for the compositions of the invention.

The present invention represents a specific advance over the sodium aluminosilicate glasses of the prior art by providing sodium aluminosilicate and sodium silicate glass compositions containing specified critical proportions of tantalum oxide to unexpectedly extend the range compositions which can be effectively used in measuring sodium ions in the presence of other monovalent cations such as $K^+$ and $NH_4{}^+$ as well as enhance the sensitivity to such measurements. The affect of $H^+$ can be minimized by carrying out such measurements at pH above 7.

For practical utility, in a sodium ion selective electrode, the glasses of U.S. Pat. No. 2,829,090 are limited to compositions wherein the $Al_2O_3$ to $Na_2O$ ratio (mole % basis) is at least 1.0. The glasses of the subject case have $Al_2O_3$ to $Na_2O$ ratios of less than 1.0. These modifications have provided glasses with generally lower melting and working temperatures than those in the prior art sodium oxide-alumina-silica ternary system and, most importantly, when made into electrodes the sodium ion to potassium ion selectivity or sensitivity is increased.

In attaining the objectives of the present invention, one feature resides in a glass composition for use in a sodium selective electrode consisting essentially of:

| Component | Mole % |
| --- | --- |
| $Na_2O$ | 5–25% |
| $Al_2O_3$ | 0–20% |
| $Ta_2O_5$ | 1–10% |
| $SiO_2$ | 60–82% |
| wherein $\frac{Ta_2O_5 + Al_2O_3}{Na_2O} \geq 0.2$ | |

For efficiency and economy, the glass compositions consist essentially of:

| Component | Mole % |
| --- | --- |
| $Na_2O$ | 10–20% |
| $Al_2O_3$ | 2–15% |
| $Ta_2O_5$ | 2–8% |
| $SiO_2$ | 65–80% |
| wherein $1 \geq \frac{Ta_2O_5 + Al_2O_3}{Na_2O} \geq 0.2$ | |

In addition to the specifically named components, the glass composition can contain minor proportions (e.g. up to about 3 mole%) of other glass forming or modifying components or refining agents such as calcium oxide, barium oxide, rare earth oxides, or batch material impurities so long as these ingredients do not detrimentally affect the selectivity of the glass toward the sodium ion.

It is recognized that the use of tantalum oxide is incidentally disclosed in lithia silicate glasses in U.S. Pat. Nos. 2,444,845; 2,497,235; and 3,713,992, but these lithia silicate compositions are quite different from the sodium containing glasses of invention.

The techniques for melting and refining the glass compositions of invention are well established in the art and no unusual techniques are required. Suffice it to say that conventional high purity (e.g. reagent grade) batch material are usually melted in refractory vessels such as platinum to minimize the concentration of undesirable impurities. Electric or gas fired furnaces in an air atmosphere at temperatures of 1600°–1700° C are quite satisfactory.

The glass compositions described above can be used as the glass sensing membrane of any practical shape and design in the so-called "glass electrode". For instance, glass electrodes having a bulbous sensing membrane as disclosed in U.S. Pat. Nos. 2,809,090 or 3,649,505 can be formed; glass electrodes having disc shaped sensing membrane as disclosed in U.S. Pat. 3,806,440 can be formed; or a wide variety of other shapes and sizes of sensing membranes such as disclosed in U.S. Pat. No. 2,756,203 or the text "Electrometric pH Determinations" by Roger G. Bates (John Wiley & Sons, Inc. New York) can be employed. The term "sensing membrane" is used herein consistent with its usage in potentiometric electrode technology, and is intended to embrace a flat, bulbous or other curved electrode tip, which provides a pair of surfaces between which change transfer is affected.

Similarly, the technique for calibration and measurement of sodium ions using the electrodes of the present invention are well established in the art such as described in the patents and publications mentioned above.

Other objectives and features of the present invention will become more apparent from the following description drawing which is a schematic representative of equipment for use in practicing the present invention.

Referring now to FIG. 1 conventional equipment is illustrated for measuring cation concentration or activity and employing one embodiment of an otherwise conventional glass electrode 10 with a sensing membrane 11 made of a glass composition of invention. The glass electrode 10 is electrically connected to a standard half-cell electrode 12, such as saturated KCl calomel, or silver-silver chloride electrode by means of a high impedance, potentiometer such as a conventional laboratory "pH meter" as described in the Bates text described above. Electrodes 11 and 12 are shown as being immersed in a vessel of aqueous test specimen.

The potentiometer can be calibrated with known aqueous solutions containing known concentrations of sodium ion as is well known in the art, and then the $Na^+$ concentration of unknown solutions can be determined directly by subjecting the calibrated glass electrode and reference electrode to the unknown solutions according to the usual procedure. For example, the equation described above can be simplified (as in U.S. Pat. No. 2,829,090) for mixtures having a wide range of pH (e.g. approximately 3 to 11).

$$E = E° + RT/F \ln [(Na^+) + K_{NaK}(K^+)]$$

wherein:
 E = measured E.M.F.
 E° = standard potential
 R = ideal gas equation constant
 T = absolute temperature
 F = Faraday constant
 $(Na^+)$ and $(K^+)$ = activity of the ionic species $Na^+$ and $K^+$, respectively
 $K_{NaK}$ = empirical constant for a given glass composition and ionic pair $Na^+$ and $K^+$.

In the examples that follow, all percentages are mole percentages, and all temperatures are in ° C unless otherwise stated.

EXAMPLE 1

A glass composition consisting essentially of:

| Component | Mole % |
|---|---|
| $Na_2O$ | 13.0 |
| $Al_2O_3$ | 5.2 |
| $SiO_2$ | 75.8 |
| $Ta_2O_5$ | 6.0 |
| wherein $\frac{Ta_2O_5 + Al_2O_3}{Na_2O} = 0.86$ | | is prepared by melting appropriate proportions of reagent grade batch materials silica, alumina, sodium carbonate, and tantalum pentoxide in a platinum vessel, in an electric furnace under an air atmosphere at a temperature of 1620° to 1670° C for 21 hours. The molten glass is periodically manually stirred during melting to assist melting. The resulting molten glass has a faint yellow-amber coloration.

After melting, the molten glass is poured as a slab into a steel mold and annealed at 650° C for 1 hour. The resulting glass has the following characteristics:
 Fiber Softening Point — 998° C
 Annealing Point — 776° C
 Strain Point — 711° C
 Volume Resistivity — $1.2 \times 10^{10}$ ohm-cm.

A glass electrode is prepared by remelting the glass prepared above and collecting a gob of the molten glass on a chemically durable, borosilicate glass stem. The stem is in the form of a thin walled tube having an outside diameter of about ⅓ inch. The molten glass gob is then blown to form a bulbous sensing membrane on the borosilicate glass stem.

The resulting glass electrode is filled with a 0.1N sodium chloride electrolyte solution and a Ag/AgCl electrode is immersed in it. The assembled electrode is connected to a conventional high impedance potentiometer (i.e. an Orion Model 801 pH meter) along with a standard silver/silver chloride reference electrode. The ion-selective and reference electrode are immersed in sodium chloride solutions which vary in concentration from $1 \times 10^{-1}$ to $1 \times 10^{-5}$ Molar. The pH is adjusted to 12 for each solution with calcium hydroxide. The electromotive force, EMF, or potential is measured for the solutions and recorded in millivolts. A plot of the logarithm of the sodium ion concentration versus the electrode potential provides a straight line with a slope of 58 mv which indicates Nerstian response. This plot is used as a calibration graph for determining the sodium ion concentration of solutions containing unknown amounts of sodium.

The relative sensitivity of this glass electrode for sodium ions in comparison to potassium and ammonium ions is determined from measurements of electrode potentials produced by solutions of sodium chloride, potassium chloride, and ammonium chloride. In this procedure, 0.10 Normal solutions of NaCl, KCl and $NH_4Cl$, [the latter adjusted to pH 7.0 with tris (hydroxymethyl) aminomethane (TRIS)] give EMF responses of 84.6, −97.5 and −141.3 millivolts respectively. This data is used to calculate relative cation sensitivities of the electrode following a procedure described in U.S. Pat. No. 2,829,090.

By this technique the glass electrode is found to be about 1400 times more sensitive to $Na^+$ ions than $K^+$ ions [i.e. $K_{KNa}$ = 1400] and 8,000 times more sensitive to $Na^+$ ions than $NH_4+$ ions [i.e. $K_{NH4Na}$ = 8000]. In a similar manner the electrode potential produced by a TRIS solution at pH 8.2 is found to be −161.0 mV. Using the same calculation procedure, the electrode is approximately 1100 times more sensitive to hydrogen ions than sodium ions [i.e. $K_{HNa} = 1.1 \times 10^{-3}$] but this is not a problem in sodium ion determinations at elevated pH.

CONTROL

The importance of $Ta_2O_5$ in glasses of invention is demonstrated preparing a glass electrode like that of Example 1 using a sensing membrane having the same mole % of $Na_2O$ and $Al_2O_3$ but no $Ta_2O_5$. Thus the glass composition is:

$Na_2O$ — 13.0%
$Al_2O_3$ — 5.2%
$SiO_2$ — 81.8%

The glass is used to prepare an electrode as in Example 1 and electrode potential measurements are made of 0.10 Normal solutions of NaCl, KCl and $NH_4Cl$. Using the calculation procedures of Example 1 $K_{KNa} = 3$ and $K_{NH_4Na} = 90$.

EXAMPLE 2

The tantalum oxide containing glass compositions of the present invention generally have lower melting and working temperatures then the sodium aluminosilicate glass compositions of the prior art for compositions having similar ion selectivity ratios. Comparison is made to a sodium ion selective glass having the preferred composition of U.S. Pat. No. 2,829,090. All selectivity measurements are made as described in Example 1.

|  | Glass A | Glass B | Prior Art |
| --- | --- | --- | --- |
| $Na_2O$ | 18 | 13.0 | 11 |
| $Al_2O_3$ | 3.6 | 5.2 | 18 |
| $SiO_2$ | 70.4 | 77.8 | 71 |
| $Ta_2O_5$ | 8.0 | 4.0 |  |
| Selectivity $K_{KNa}$ | 480 | 700 | 500 |
| Selectivity $K_{NH_4Na}$ | 2000 | 6000 | 3000 |
| Fiber Softening Pt. | 921° C | 940° C | 1085° C |
| Annealing Pt. | 668° | 690° | 790° |
| Strain Pt. | 610° | 630° | 726° |

EXAMPLE 3

To further demonstrate the principles of the present invention, several glass compositions containing various proportions of $Ta_2O_5$ are prepared and evaluated by the procedures of Example 1. The results are set forth below in Table I.

Table II presents the properties of several prior art sodium aluminosilicate glasses for the purpose of comparison.

Table I

| Glass | A | B | C | D | E | F | G |
| --- | --- | --- | --- | --- | --- | --- | --- |
| $Na_2O$ | 23.0 | 18.0 | 20.0 | 13.0 | 15.0 | 18.0 | 18 |
| $Al_2O_3$ | 4.6 | 3.6 | 10.0 | 10.0 | 12.0 | 15.0 | 3.6 |
| $SiO_2$ | 70.4 | 76.4 | 68.0 | 74.0 | 70.0 | 64.0 | 74.4 |
| $Ta_2O_5$ | 2.0 | 2.0 | 2.0 | 3.0 | 3.0 | 3.0 | 4.0 |
| $Ta_2O_5/Na_2O$ | 0.087 | 0.11 | 0.10 | 0.23 | 0.20 | 0.167 | 0.22 |
| $Al_2O_3/Na_2O$ | 0.20 | 0.2 | 0.5 | 0.77 | 0.80 | 0.83 | 0.20 |
| $\frac{Ta_2O_5+Al_2O_3}{Na_2O}$ | 0.287 | 0.311 | 0.6 | 1 | 1 | 1 | 0.42 |
| Selectivity Factor | | | | | | | |
| $K_{KNa}$ | 4.2 | 10 | 200 | 400 | 400 | 400 | 33 |
| $K_{NH_4Na}$ | 110 | 400 | 1000 | 2000 | 2000 | 2000 | 900 |
| $K_{HNa}$ | $1 \times 10^{-3}$ | $2 \times 10^{-3}$ |  |  |  |  | $1 \times 10^{-3}$ |
| Fiber Softening Point |  |  | 836° C |  |  |  |  |
| Annealing Point |  |  | 612° |  |  |  |  |
| Strain Point |  |  | 563° |  |  |  |  |
| Glass | H | I | J | K | L | M | N | O |
| $Na_2O$ | 13.0 | 13.0 | 20.0 | 13.0 | 10.0 | 18.0 | 20.0 | 13.0 |
| $Al_2O_3$ | 2.6 | 5.2 | 10.0 | 5.2 | 2.0 | 3.6 | 4.0 |  |
| $SiO_2$ | 80.4 | 77.8 | 65.0 | 75.8 | 82.0 | 70.4 | 68.0 | 81.8 |
| $Ta_2O_5$ | 4.0 | 4.0 | 5.0 | 6.0 | 6.0 | 8.0 | 8.0 | 5.2 |
| $Ta_2O_5/Na_2O$ | 0.31 | 0.31 | 0.25 | 0.46 | 0.60 | 0.44 | 0.40 | 0.4 |
| $Al_2O_3/Na_2O$ | 0.20 | 0.40 | 0.50 | 0.40 | 0.20 | 0.20 | 0.20 |  |
| $\frac{Ta_2O_5+Al_2O_3}{Na_2O}$ | 0.51 | 0.71 | 0.75 | 0.86 | 0.80 | 0.64 | 0.60 | 0.4 |
| Selectivity Factor | | | | | | | | |
| $K_{KNa}$ | 300 | 700 | 400 | 1300 | 1100 | 480 | 1000 | 220 |
| $K_{NH_4Na}$ | 1000 | 6000 | 2000 | 8000 | 3000 | 2000 | 1000 | 1000 |
| $K_{HNa}$ | $1 \times 10^{-3}$ | $2 \times 10^{-3}$ |  | $2 \times 10^{-3}$ | $2 \times 10^{-3}$ |  |  |  |
| Fiber Softening Point | 889° C | 940° C | 910° C | 998° C | 997° C | 921° C | 896° C | 887° C |
| Annealing Point | 649° | 690° | 702° | 776° | 798° | 668° | 548° | 714° |
| Strain Point | 589° | 632° | 655° | 711° | 740° | 610° | 491° | 664° |

Table II

| | P | Q | R | S | T |
|---|---|---|---|---|---|
| $Na_2O$ | 20.0 | 23 | 18 | 13.0 | 11 |
| $Al_2O_3$ | 10.0 | 4.6 | 3.6 | 5.2 | 18 |
| $SiO_2$ | 70.0 | 72.4 | 78.4 | 81.8 | 71 |
| $\frac{Al_2O_3}{Na_2O}$ | 0.5 | 0.2 | 0.2 | 0.4 | 1.64 |
| $K_{KNa}$ | 30 | 0.6 | 1.5 | 3 | 500 |
| $K_{NH_4Na}$ | 300 | 2.8 | 33 | 90 | 3000 |
| $K_{HNa}$ | | | $1 \times 10^{-3}$ | | $1 \times 10^{-3}$ |
| Fiber Softening Point | 887° C | | | 791° C | |
| Annealing Point | 714° | | | 693° | |
| Strain Point | 664° | | | 643° | |

From the foregoing comparative data, it is readily apparent that the present invention provides a new family of sodium specific glass compositions which have improved selectivity as a result of the inclusion of specified proportions of tantalum oxide. For convenience in disclosure, all of the patents and publications mentioned herein are incorporated by reference.

Having thus described the invention, what is claimed is:

1. In an electrode having a glass sensing membrane the improvement wherein said sensing membrane is selectively responsive to sodium ions in an ionic mixture containing sodium and other monovalent cations and has a composition consisting essentially of:

| Component | Mole % |
|---|---|
| $Na_2O$ | 5–25% |
| $Al_2O_3$ | 0–20% |
| $Ta_2O_5$ | 1–10% |
| $SiO_2$ | 60–82% | wherein $\frac{Ta_2O_5 + Al_2O_3}{Na_2O} \geq 0.2$.

2. The glass electrode of claim 1 wherein said sensing membrane has a composition consisting essentially of:

| Component | Mole % |
|---|---|
| $Na_2O$ | 10–20% |
| $Al_2O_3$ | 2–15% |
| $Ta_2O_5$ | 2–8% |
| $SiO_2$ | 65–80% | wherein $1 \geq \frac{Ta_2O_5 + Al_2O_3}{Na_2O} \geq 0.2$.

* * * * *